MAGNETICALLY COUPLED IMPLANTABLE SERVOMECHANISM

Original Filed April 14, 1969

United States Patent Office

Re. 27,661
Reissued June 5, 1973

27,661
MAGNETICALLY COUPLED IMPLANTABLE SERVOMECHANISM

Lee R. Bolduc, St. Louis Park, and George F. Schwoboda, New Brighton, Minn., by Medtronic, Inc., assignee Original No. 3,569,894, dated Mar. 9, 1971, Ser. No. 815,857, Apr. 14, 1969. Application for reissue Oct. 18, 1971, Ser. No. 190,193
Int. Cl. H01c *1/12*
U.S. Cl. 338—12 8 Claims

Matter enclosed in heavy brackets [ ] appears in the original patent but forms no part of this reissue specification; matter printed in italics indicates the additions made by reissue.

ABSTRACT OF THE DISCLOSURE

A magnetically coupled servomechanism wherein a remote magnetic device is driven by a motor and is magnetically coupled to a second rotatable magnetic device in a hermetically sealed unit for implantation in the body of an animal, which device imparts its resultant motion to an [output] *imput* shaft connected to a stepdown gear train having an output shaft which imparts torque to the element it is desired to rotate. The input shaft, gear train and output shaft are also in the hermetically sealed unit. The output shaft shaft may be electrically insulated from the element to be driven, such as a potentiometer. The mechanism may be used to selectively drive more than one element, in which case a drive device is slideably mounted on the output shaft of the gear train, to be selectively slid longitudinally along the shaft to couple with the selected element for driving.

BACKGROUND OF THE INVENTION

This invention is concerned with servomechanisms, and more specifically with a magnetically coupled, hermetically sealed, servomechanism for the remote control of selected elements, particularly elements implanted in the body of an animal. Servomechanisms are well known in the art, and there are many and various such mechanisms. One problem of the field of servomechanism is to remotely control and [an] element from an actuator which has no physical connection to the control device. The apparatus of this invention utilizes magnetic coupling to avoid physical connection between actuator and control device. Similar coupling has been described in "A New Miniature Pump for the Treatment of Hydrocephalus," by George D. Summers and Ernest S. Mathews, JAAMI, May/June [1964] *1967*, pp. 8–16; and "Magnetics for Power and Control of Body Implants," by George D. Summers, Biomedical Sciences Instrumentation, vol. 4, pp. 293–302.

Another problem which arises in servomechanism is accuracy between the remote actuator and the control device to impart a specific reaction from the element being controlled. The apparatus of this invention provides such control through a stepdown gear train which has a high stepdown ratio between input turns and output turns to improve accuracy of positioning at the output shaft. The structure of this invention and the operation providing the advantages will be better understood from the description which follows.

SUMMARY OF THE INVENTION

Briefly described, the apparatus of this invention comprises: a remote actuator including a motor having a rotatable shaft connected to a magnetic device. The control device which is driven by the remote actuator includes another magnetic device connected to a rotatable input shaft, which shaft is in turn connected to a gear train, preferably a stepdown gear train, that has an output shaft.

The output shaft is then connected through coupling means to the element which is to be controlled to impart torque thereto. The control device is encased in a sealed unit to make it substantially impervious to body fluids and tissue.

In one of its embodiments, the apparatus of this invention can drive a selected one of a pair of elements. This is accomplished by connecting a drive device to the output shaft of the gear train such that the drive device can slide longitudinally on the shaft but is connected [tom] *to* impart the torque from the shaft. By properly positioning the drive device through sliding, it couples with members on each of the pair of elements to drive the selected one of the elements. When the element to be controlled is electrical, the output shaft is insulated therefrom.

DESCRIPTION OF THE PREFERRED EMBODIMENTS

Figure 1:
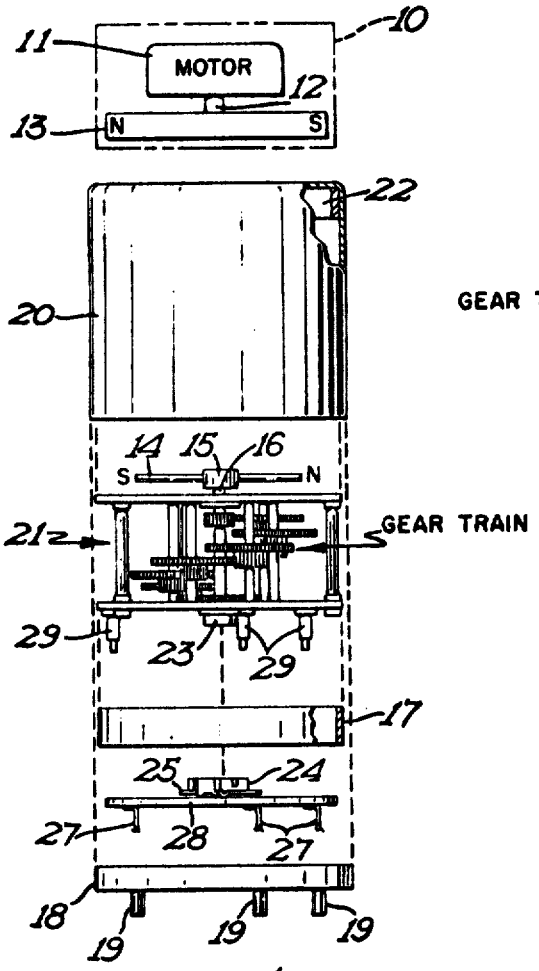
FIG. 1 is a side plane view of a diagrammatical representation of a first embodiment of the apparatus of this invention.

It should first be recognized that the diagrammatical representation of FIGS. 1–4 of the drawing are not intended to be in scale and are in diagram form to facilitate ease of understanding and description. No scaled showing is intended, and in fact, scale varies from one portion to another of each figure. For example, the magnet of the remote actuator described below will usually be much larger in size than the control magnet described below, though for ease of understanding the two magnets are shown in the drawings as about the same size.

Referring first to FIG. 1, there is shown in dotted lines a remote actuator indicated generally as 10. Actuator 10 includes a motor 11 having a rotatable shaft 12 which is connected to a magnet 13, here shown as a bar magnet having a north and south pole. Preferably in an actual embodiment as opposed to the diagrammatical showing of FIG. 1, motor 11 will be a reversible type, and have switch means for selecting the direction of rotation. Also, it would be desirable to have counting means attached to motor 11 or shaft 12 to count the number of turns in either direction of magnet 13.

Also shown in FIG. 1 is another magnet 14 here shown as a bar magnet having north and south poles. Magnet 14 is connected by a coupling device 15 to a rotatable input shaft 16. Shaft 16 is connected to a gear train 21, having a plurality of interconnected gears, and an output shaft 23. Preferably, gear train 21 is a stepdown gear train, that is, a plurality of rotational inputs into gear train 21 at shaft 16 will result in an output of fewer turns of shaft 23.

Output shaft 23 is adapted to be connected to a coupling device 24, which coupling device 24 is in turn connected to a movable portion 25 of an element 28 it is desired to control. In the embodiment of FIG. 1 element 28 can be, [fore] *for* example, a potentiometer having a moveable wiper arm 25. Potentiometer 28 has a plurality of leads 27. Element 28 is connected to gear train 21 by supports 29. Output shaft 23 is connected to wiper arm 25 by an electrically insulating material, preferably coupling device 24, to electrically isolate gear train 21 and potentiometer 28.

In FIG. 1 there is also shown a case 20, of a nonmagnetic material. Case 20 is closed on all but its bottom side and is adapted to receive gear train 21 as it is connected to magnet 14 and potentiometer 28 for hermetic sealing. A spacer 22 is provided in case 20 for spacing rotatable magnet 14 from the sides of case 20. Spacer 22 is preferably a nonmagnetic, electrically insulating material such as polyethylene, nylon, Teflon, or Delrin. A header 18 is provided for sealing the bottom side of case 20. Another spacer 17 is provided to space header 18 from potentiometer 28. Header 18 includes flanged apertures 19 through which leads 27 are passed to provide electrical access to the hermetically sealed potentiometer 28. Apertures 19 are electrically insulated from the sides of header 18. When header 18 is in place at the bottom side of case [10] *20* it is soldered or welded to case 20, to provide a hermetic seal. Apertures 19 are also sealed, for example by soldering. If desired, another sealable aperture can be provided in header 18 through which the air in case 20 can be drawn out to be replaced with an inert gas, such as helium. It has been found preferable to insert the inert gas at a pressure substantially equal to that of the atmosphere around case 20.

In operation, motor 11 can be turned on to rotate shaft 12 and thus magnet 13. Magnet 13 is held sufficiently close to magnet 14 to provide magnetic coupling and the moving flux lines of magnet 13 will affect magnet 14 to cause it to rotate also. The rotation of magnet 14 will be felt through coupler 15 to apply torque to input shaft 16. The rotation of shaft 16 will actuate gear train 21, and result in the rotation of output shaft 23 at a much lower speed than the rotation of input shaft 16. The torque from shaft 23 will be felt through coupling device 24 to actuate the moveable portion of element 28, described above as a wiper arm of a potentiometer, for example.

One use to which the apparatus of FIG. 1 is highly adapted is for control of electrical signals in an implantable device for providing electrical stimulation to various parts of the human body. In such use, remote actuator 10 of FIG. 1 would be external to the body and hermetically sealed case 20 as shown and described in FIG. 1 could be encased in a substance substantially inert to body fluids and tissue and implanted in the body as a portion of an electrical stimulating device. Element 28 can be, for example, a potentiometer, and the electrical output characteristics of the implanted device can be changer by using remote actuator 10 to cause a movement of the wiper arm 25 of potentiometer 28. High accuracy can be obtained by having a large stepdown turns ratio in gear train 21. One such device has been built and tested which has a 1,500 to 1 ratio in gear train 21, and has proven to provide a highly accurate motion of wiper arm 25 of potentiometer 28. This high stepdown ratio provides a device which requires a continuous organized rotary motion of a magnetic field to obtain movement of wiper arm 25. It thereby provides protection again accidental adjustment of potentiometer 28 by random magnetic fields.

Figure 2:
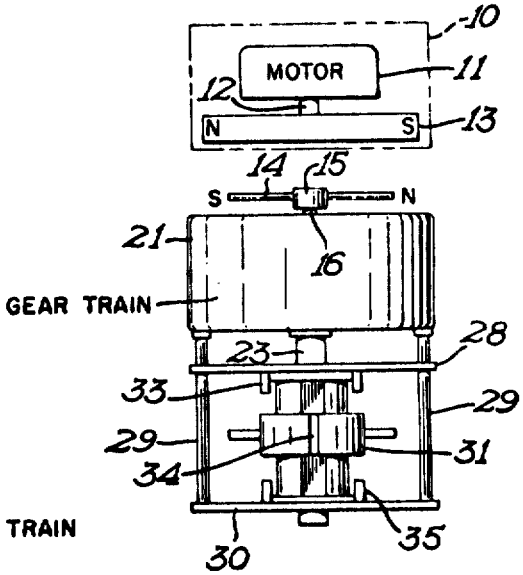
FIG. 2 is a side plane view of a diagrammatically representation of a second embodiment of the apparatus [of the apparatus] of the invention.

Referring now to FIG. 2, there is shown a variation of the preferred embodiment of FIG. 1 wherein two separate elements can be individually controlled by the apparatus of this invention. There is again shown a remote actuator 10 having a motor 11, shaft 12 and magnet 13. A magnet 14 is again coupled through a device 15 to rotatable shaft 16 which is connected to a gear train 21, here shown separately encased. Gear train 21 has an output shaft 23 which passes through but is not directly connected to a pair of elements to be controlled 28 and 30. Elements 28 and 30, which can again be potentiometers for example, are connected by supports 29 to gear train 21. At least a portion of shaft 23 is splined, and has connected to it a drive member 31 which is also splined to mate with shaft 23. The mounting of member 31 on shaft 23 is such that shaft 23 will impart torque to drive member 31, but member 31 will be free to slide longitudinally on shaft 23. Further, the location of drive member 31 is between elements 28 and 30. Element 28 has teeth 33 connected to its moveable portion and extending toward member 31. Element 30 has teeth 35 connected to its moveable portion and extending toward member 31. Member 31 has a plurality of slots 34 adapted to engage either teeth 33 or teeth 35. The apparatus shown in FIG. 2 is adapted to be encased in the same manner as shown and described in FIG. 1.

Figure 3:
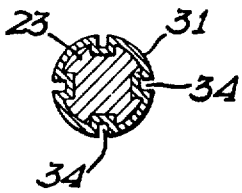
FIG. 3 is a sectional view of a portion of the apparatus of FIG. 2.

In FIG. 3 there is shown a cross-sectional view of splined shaft 23 and splined member 31, in their mating condition. A plurality of slots 34 are also shown.

The operation of the apparatus of FIG. 2 is similar to that described above for the apparatus of FIG. 1 with the addition that by selective tilting of the apparatus of FIG. 2 member 31 will slide on shaft 23 to engage teeth 33 of element 28 for operation thereof, or to engage teeth 35 of element 30 for operation thereof. Thus, either element 28 or element 30 can be selected for control from remote actuator 10.

Figure 4:
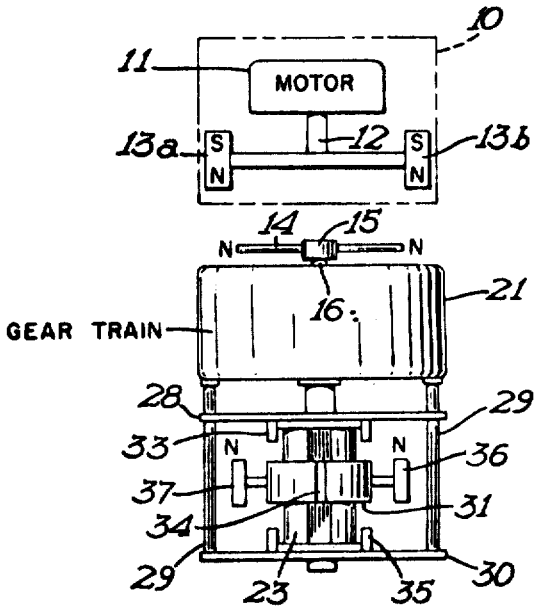
FIG. 4 is a side [plan] *plane* view of a diagrammatical representation of a variation of the embodiment of FIG. 2.

Referring now to FIG. 4 there is shown a further embodiment of the apparatus of FIG. 2, which includes all of the apparatus mentioned in the above description of FIG. 2 including a splined member 31 which is slideably mounted on splined shaft 23. However, in the embodiment of FIG. 4 magnet 13 is replaced by a pair of magnets 13a and 13b each having a north and a south pole. The construction of remote actuator 10 is such that a selection can be made to have both north poles of magnets 13a and 13b in an operative position with respect to magnet 14, or alternatively, to have both sound poles of magnets 13a and 13b in an operative position with respect to magnet 14. Member 31 is shown as including a magnetized portion which may be a pair of bar magnets 36 and 37 as shown, or a circular rim of magnetic material. As shown in FIG. 4, the upper portion of magnets 36 and 37 constitutes a north pole in both cases, though the poles could be south poles as long as both were similar.

In operation, drive member 31 will actuate either of elements 28 or 30, by engaging their respective of teeth 33 or 35, depending on whether it is pulled up shaft 23 by magnets 13a and 13b, or repelled downward along shaft 23 by magnets 13a and 13b. With the poles of magnets 13a and 13b in the position as shown in *FIG. 4, the north poles of magnets 13a and 13b would repel the north poles of magnets 36 and 37 to slide drive member 31 downward to connect with teeth 35. If magnets 13a and 13b were selectively reversed such that their south poles were in the operative position, the north poles* [FIG. 4, the north **13*b* would repel the north poles of 31 downward to connect reversed such with teeth 35. If magnets 13*a* and 13*b* were selectively reversed such that their south poles were in the operative position the north poles] of magnets 36 and 37 would cause drive member 31 to slide upward on shaft 23 to engage teeth 33. Thus, in this preferred embodiment, a selection of elements to be driven can be made by a simple manipulation at remote actuator 10 to determine which poles of magnets 13a and 13b will be in the operative position with respect to magnet 14. It will be apparent also that a single magnet 13 could be used which is capable of having only its north or its south pole in operative relation with respect to magnet 14**.

From the above description it will be apparent that various embodiments other than those shown can be built within the bounds of the invention described herein. For example, shaft 23 in any of FIGS. 1–4 could extend to couple to a plurality of elements such as 28, which plurality could be greater than the two shown. Also, if speed rather than accuracy is desired, gear train 21 could be a step-up type train to provide a greater number of revolutions at output shaft 23 than is provided in input shaft 16. Or, for example, gear train 21 could be a one-one ratio gear train if speed and greater accuracy are not desired.

We claim:

1. Magnetic servo apparatus for implantation in the body of an animal and adapted to be driven by a remote rotating magnetic field, comprising:

gear means having an input shaft and an output shaft, said gear means having a stepdown ratio between turns of said input shaft and turns of said output shaft;

magnet means connected to said input shaft for rotation thereof when said magnet means is in the rotating magnetic field;

mechanically adjustable electrical means;

electrically insulating means connecting said output shaft to said electrical means for selective adjustment thereof;

electrically conductive lead means connected to said electrical means;

nonmagnetic case means;

*said gear means having a stepdown ratio sufficient to substantially protect against accidental adjustment of said electrical means by random magnetic fields and to permit substantially accurately positioning at said output shaft;* and said gear means, said magnet means, said electrical means, *said* electrically insulating means and a portion of said lead means hermetically sealed in said case means.

2. The apparatus of claim 1 in which said magnet means comprises: at least one bar magnet having north and south magnetic poles at opposite extremities.

3. The apparatus of claim 1 including: a pair of said electrical means connected to said output shaft by electrically insulating means; drive means mounted on said output shaft; said drive means mounted to receive torque from said output shaft and to slide longitudinally thereon when said output shaft is selectively tilted; and said drive means adapted to selectively couple to electrically insulating coupling means on either one of said pair of electrical means, dependent on the longitudinal position of said drive means on said output shaft.

4. The apparatus of claim 3 in which said drive means includes further magnet means adapted to be selectively attracted or repelled by the remote magnetic field, for selective placement longitudinally along said output shaft.

5. The apparatus of claim 3 in which: said drive means and at least a portion of said output shaft have mating splines for interconnection allowing relative longitudinal movement only.

6. The apparatus of claim 1 including: nonmagnetic spacer means in said case means for spacing said magnet means from said case means for free rotation of said magnet means.

7. The apparatus of claim 6 including: header means mounted on said case means for sealing said case means and including sealable apertures through which pass said lead means; and further spacer means for spacing said header means from said electrical means.

8. The apparatus of claim 1 in which: the atmosphere in said case means comprises an inert gas at substantially the same pressure as the atmosphere external to said case means.

References Cited

The following references, cited by the Examiner, are of record in the patented file of this patent or the original patent.

UNITED STATES PATENTS

| | | | |
|---|---|---|---|
| 2,467,497 | 4/1949 | Ramos | 338—12 |
| 2,537,733 | 1/1951 | Brenner | 338—12 |
| 2,906,838 | 9/1959 | Delghton | 335—75 |
| 2,906,983 | 9/1959 | Jenney | 338—116 |

CLARENCE L. ALBRITTON, Primary Examiner

U.S. Cl. X.R.

335—75; 338—116